(12) United States Patent
Kolen et al.

(10) Patent No.: US 9,878,152 B2
(45) Date of Patent: Jan. 30, 2018

(54) ELECTRICAL MUSCLE STIMULATION (75) Inventors: Alexander Franciscus Kolen, Eindhoven (NL); Agathe Melanie Puszka, Fontaine (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 64 days.

(21) Appl. No.: 13/508,060

(22) PCT Filed: Oct. 29, 2010

(86) PCT No.: PCT/IB2010/054901
§ 371 (c)(1),
(2), (4) Date: May 4, 2012

(87) PCT Pub. No.: WO2011/055282
PCT Pub. Date: May 12, 2011

(65) Prior Publication Data
US 2012/0226330 A1    Sep. 6, 2012

(30) Foreign Application Priority Data
Nov. 5, 2009    (EP) .................... 09175147

(51) Int. Cl.
*A61N 1/36* (2006.01)
*A61B 5/0488* (2006.01)
(Continued)

(52) U.S. Cl.
CPC ........ *A61N 1/36003* (2013.01); *A61B 5/0488* (2013.01); *A61B 5/11* (2013.01);
(Continued)

(58) Field of Classification Search
CPC ........ A61N 1/36; A61N 1/36003; A61B 5/04; A61B 5/0488; A61B 5/11
(Continued)

(56) References Cited

U.S. PATENT DOCUMENTS 3,204,637 A * 9/1965 Frank et al. .................... 607/49
4,249,537 A * 2/1981 Lee et al. ........................ 607/64
(Continued)

FOREIGN PATENT DOCUMENTS

WO    WO9924111 A1    5/1999
WO    WO2007017778 A2    2/2007
(Continued)

OTHER PUBLICATIONS

Popovic-Bijelic et al., "Multi-Field Surface Electrode for Selective Electrical Stimulation." Artificial Organs, vol. 29, No. 6, International Center for Artificial Organs and Transplantation, pp. 448-452, 2005.

*Primary Examiner* — Christopher A Flory
(74) *Attorney, Agent, or Firm* — Larry Liberchuk (57) ABSTRACT The invention relates to a method and an apparatus for electrical stimulation of muscle tissue. Electrodes (12) of an electrode array (13) are activated in accordance with a sequence of activation patterns, each pattern defining a subset of the electrodes (12) to be activated, each subset consisting of at least one electrode (12), by providing an electrical muscle stimulation signal to the muscle tissue via the subset of electrodes (12). Alternately with said activating of electrodes (12), a response signal associated with the respective activation pattern is received from a sensor (30; 12). Optionally, at least one electrode (12) is then selected for stimulation, corresponding to a location determined as being suitable for stimulation, and the muscle tissue is stimulated. The process may be repeated in order to track the location suitable for stimulation in a dynamic situation. Optionally, the orientation of body part is estimated from the measured response signals.

9 Claims, 4 Drawing Sheets (51) Int. Cl.
*A61B 5/11* (2006.01)
*A61H 39/00* (2006.01)
*A61H 39/02* (2006.01)

(52) U.S. Cl.
CPC ........... *A61H 39/002* (2013.01); *A61H 39/02* (2013.01); *A61N 1/36014* (2013.01); *A61H 2201/5084* (2013.01); *A61H 2230/08* (2013.01); *A61H 2230/62* (2013.01); *A61N 1/36007* (2013.01)

(58) Field of Classification Search
USPC ................ 600/547; 607/46, 48, 49, 72, 116
See application file for complete search history.

(56) References Cited

U.S. PATENT DOCUMENTS

| | | | | |
|---|---|---|---|---|
| 4,411,268 A | * | 10/1983 | Cox | .................. 607/9 |
| 4,619,266 A | | 10/1986 | Hodgson | |
| 4,811,742 A | | 3/1989 | Hassel | |
| 4,909,255 A | * | 3/1990 | Farin | ............... 607/67 |
| 4,917,093 A | * | 4/1990 | Dufresne et al. | ............... 607/62 |
| 5,480,416 A | * | 1/1996 | Garcia et al. | .................. 607/36 |
| 5,527,357 A | * | 6/1996 | Springer, Jr. | .................. 607/140 |
| 5,843,155 A | * | 12/1998 | Axelgaard | .................... 607/152 |
| 5,904,712 A | * | 5/1999 | Axelgaard | .................... 607/148 |
| 6,002,957 A | * | 12/1999 | Finneran | ...................... 600/382 |
| 6,014,588 A | * | 1/2000 | Fitz | ...................... 607/46 |
| 6,038,485 A | * | 3/2000 | Axelgaard | .................... 607/148 |
| 6,083,252 A | * | 7/2000 | King et al. | ...................... 607/70 |
| 6,110,098 A | * | 8/2000 | Renirie et al. | ................... 600/16 |
| 6,128,536 A | * | 10/2000 | Noack et al. | ................... 607/39 |
| 6,141,585 A | * | 10/2000 | Prutchi et al. | .................... 607/8 |
| 6,876,883 B2 | | 4/2005 | Hurtado | |
| 7,493,157 B2 | * | 2/2009 | Gozani et al. | ................. 600/546 |
| 7,826,900 B2 | * | 11/2010 | Stellar | ..................... A61B 5/05 607/46 |
| 2001/0000187 A1 | * | 4/2001 | Peckham et al. | ................. 607/48 |
| 2002/0183647 A1 | * | 12/2002 | Gozani et al. | ................. 600/554 |
| 2004/0225211 A1 | * | 11/2004 | Gozani et al. | ................. 600/382 |
| 2006/0241717 A1 | * | 10/2006 | Whitehurst et al. | ........... 607/45 |
| 2006/0264775 A1 | * | 11/2006 | Mills | ..................... A61B 5/0537 600/547 |
| 2006/0276702 A1 | * | 12/2006 | McGinnis | ........... A61B 5/0408 600/372 |
| 2008/0051673 A1 | * | 2/2008 | Kong | ................. A61B 5/04001 600/546 |
| 2008/0234781 A1 | | 9/2008 | Einav | |
| 2008/0288020 A1 | | 11/2008 | Einav | |
| 2009/0118790 A1 | | 5/2009 | Van Herk | |
| 2010/0004715 A1 | | 1/2010 | Fahey | |
| 2010/0069780 A1 | | 3/2010 | Schuette et al. | ................. 600/547 |
| 2012/0226330 A1 | * | 9/2012 | Kolen et al. | .................... 607/48 |
| 2013/0030277 A1 | * | 1/2013 | Fahey | ............................ 600/384 |
| 2013/0090568 A1 | * | 4/2013 | Gharib | .............. A61B 5/04001 600/546 |

FOREIGN PATENT DOCUMENTS

| | | |
|---|---|---|
| WO | WO2008005478 A2 | 1/2008 |
| WO | WO2008075250 A1 | 6/2008 |
| WO | WO2010064206 A1 | 6/2010 |

* cited by examiner

ELECTRICAL MUSCLE STIMULATION

The invention relates to the field of electrical muscle stimulation. More specifically, the invention relates to a method for providing an electrical muscle stimulation signal to body tissue that contacts muscle tissue, and to an apparatus for electrical stimulation of muscle tissue.

BACKGROUND OF THE INVENTION

Electrical stimulation or functional electrical stimulation (FES) of muscles is a well-known application e.g. in the areas of stroke rehabilitation, spinal cord injury rehabilitation, incontinence treatment, and sport enhancement treatment.

From WO 2007/017778 A2, an apparatus for electrical stimulation of muscle tissue is known that has an electrode system with an electrode array. The apparatus has an electrode selector for selecting one or more stimulating electrode pads. In one example, after the electrode system is positioned on the skin of a user, the impedance between each of the electrode pads and the skin is measured, and based on the measured impedance, one or more stimulation electrode pads are selected. In another example, stimulation electrode pads may be selected based on the area in which the muscle exhibits the lowest activity. The apparatus may be used to stimulate the muscle tissue by providing an electrical signal such that the muscle tissue alternately contracts and relaxes. Prior to stimulating the muscle tissue, a first measurement of the activity of the muscle tissue is performed, and after stimulating the muscle tissue, a second measurement of the activity of the muscle tissue is performed. Thus, the effect of the stimulation on the activity of the muscle tissue can be determined. The values for the activity determined before and after the stimulation may be outputted to a user interface.

SUMMARY OF THE INVENTION

It would be desirable to be able to find locations suitable for electrical stimulation of muscle tissue in a convenient manner and/or without having to reposition an electrode or stimulation apparatus.

It would also be desirable to be able to find a suitable location for electrical stimulation of muscle tissue while a respective muscle is activated. When a muscle is activated, an optimal location for electrical stimulation may differ from an optimal location for stimulation in a non-activated state of the muscle.

It would also be desirable to be able to find a location suitable for electrical stimulation of muscle tissue in a non-static situation, for example while a respective muscle contracts or relaxes. During contraction or relaxation of a muscle, a location suitable for stimulation of muscle tissue may move. Moving of a location suitable for stimulation of a specific muscle may also be caused by activation or contraction or relaxation of a different muscle.

It would also be desirable to be able to track the movement or changing of a location suitable for electrical stimulation of muscle tissue in a non-static situation as described.

It would be desirable to be able to improve muscle stimulation without requiring implanting of electrodes. Implanting electrodes is an invasive, costly and risky procedure and thus is limited to specific cases.

In particular, it would be desirable to be able to find a location suitable for electrical stimulation of muscle tissue with an apparatus that may be applied from external to the skin above said muscle tissue.

It would also be desirable to be able to conveniently locate a location suitable for electrical stimulation of muscle tissue in order to stimulate a specific muscle in a group of muscles.

To better address one or more of these concerns, in a first aspect of the invention, there is provided a method for providing an electrical muscle stimulation signal to body tissue that contacts muscle tissue, comprising:

positioning an electrode array comprising a plurality of electrodes in electrical contact with said body tissue;

activating said electrodes in accordance with a sequence of activation patterns, each activation pattern defining a subset of the electrodes to be activated, each respective subset consisting of at least one electrode, by providing an electrical muscle stimulation signal to said body tissue via the at least one electrode of the respective subset, and, alternately with said activating of electrodes in accordance with an activation pattern, measuring a response signal associated with the activation pattern by sensing a property of said muscle tissue, which property forms a measure for activity of said muscle tissue in response to the electrical stimulation signal provided via said at least one electrode of the activation pattern to said body tissue contacting said muscle tissue. For example, the measuring step is performed after each performing of the activating step.

Such a method allows to test different activation patterns of electrodes for their effectiveness in stimulating a target muscle tissue. Thereby, an activation pattern corresponding to a suitable location for electrical stimulation may be determined automatically. This is advantageous in particular in applications where said location may change, e.g. due to movement of the muscle tissue beneath the skin on which the electrode array is arranged. Thus, a suitable activation pattern for a muscle may determined in both static (no contraction or no change of contraction of the muscle) and dynamic (during contraction of the stimulated muscle or contraction and/or relaxation of muscle groups in same area) situations.

Furthermore, the method allows to position the electrode array with a lower degree of precision without affecting the stimulation of the muscle tissue, since for the stimulation one or more electrodes of the electrode array may be selected dependent on the measured response signals, which electrodes are present in an area suitable for providing the stimulation signal. Also, since the electrode array may be positioned with a lower degree of precision, the electrode array can be placed by a person without specialist knowledge about the muscle system. Furthermore, placing the electrode array is less time-consuming. Furthermore, comparatively small electrodes may be used for stimulating instead of e.g. a single pair of large electrodes large enough to surely cover the area suitable for stimulation. Large external electrodes can be painful due to a large current and/or voltage required for stimulation. Furthermore, large electrodes cannot target smaller muscle groups. Furthermore, large electrodes may have side effects such as stimulating another muscle or other types of nerves under the electrode (e.g. pain nerves, sensory nerves).

For example, the electrodes may be electrode pads or surface electrodes. This has the advantage of being less invasive than needle electrodes, for example.

For example, after each activating of electrodes in accordance with an activation pattern, providing of the stimulation signal ends or is stopped, and, during a stimulation pause, the response signal is measured.

In particular, said sequence of activation patterns may be a sequence of different activation patterns. By measuring the response signal associated with the respective activation pattern, an activation pattern suitable or best suitable for electrical stimulation of said muscle tissue may be determined. Thus, the suitable location or activation pattern for stimulation may be determined without repositioning the electrode array.

For example, said body tissue may comprise a skin above the muscle tissue. Alternatively, for example, said body tissue may be a part of said muscle tissue.

The steps of activating said electrodes in accordance with a sequence of activation patterns and, alternately with said activating of electrodes in accordance with an activation pattern, measuring a response signal associated with the activation pattern, will also be denoted as the "search steps" or the "search process" in the following. For example, these steps are repeated. When, for example, a suitable location for electrical stimulation moves within the area covered by the electrode array due to contraction or relaxation of a muscle, for example, the method allows to automatically track the suitable location for stimulation.

For example, said measuring of a response signal is an electromyography measuring.

Useful details of the invention are indicated in the dependent claims.

For example, the method may further comprise:

Selecting at least one of the plurality of electrodes based on the measured response signals. For example, at least one electrode suitable, in particular, best suitable, for stimulating the muscle tissue may be selected. For example, at least one electrode may be selected for stimulating the muscle tissue. For example, the at least one of the plurality of electrodes may be selected based on the magnitude of the measured response signals. However, selecting said at least one of the plurality of electrodes is not necessarily followed by stimulating the selected at least one electrode. For example, selecting at least one of the plurality of electrodes suitable for stimulation, based on the measured response signals, may be for the purpose of gathering information, such as for determining an orientation of a body part as will be described further below.

For example, based on selecting at least one electrode suitable for stimulating the muscle tissue, a position of the electrode array relative to said muscle tissue may be determined. Thus, a position of the electrode array relative to a body part may be determined. Thus, a position of a device that is in fixed positional relationship with the electrode array may be determined relative to a body part. For example, said device may be integrated with the electrode array. For example, said device may include an accelerometer. Thus, the position of the accelerometer may be determined relative to a body part. Thus, accelerometer readings may be related to movement of said body part based on the determined position of the accelerometer.

For example, said at least one of the plurality of electrodes is selected based on a criterion suitable for determining the muscle activity from the response signal, in particular, a criterion suitable for determining the highest muscle activity from the response signals. For example, said at least one of the plurality of electrodes is selected based on at least one of the criteria of:

a highest peak to peak value of the response signal,
a largest area under the curve of the response signal,
a fastest increase array of the response signal and
a fastest decrease rate of the response signal.

Without wishing to be bound to any theory, it is believed that these criteria are expressions of the magnitude of the response signals indicating the effectiveness of stimulating said muscle tissue according to the respective activation pattern. For example, said at least one of the plurality of electrodes may be selected based on a magnitude of muscle activity as represented by the measured response signals. It is believed that said criteria represent the magnitude of muscle activity in response to the electrical stimulation according to the activation pattern. Furthermore, it is believed that such activation pattern is a suitable activation pattern for stimulating the muscle tissue.

For example, selecting at least one of the plurality of electrodes based on the measured response signals may comprise comparing all response signals, or comparing the magnitude of the response signals.

For example, at least one of the plurality of electrodes may be selected by selecting at least one of the activation patterns. Furthermore, for example, a subset of the electrodes may be selected which corresponds to a combination of at least two of the activation patterns. Thus, electrodes may be selected corresponding to a combination of the most promising activation patterns for stimulation of the muscle tissue.

In one embodiment, the method further comprises:

selectively providing via said selected at least one electrode and via said body tissue an electrical muscle stimulation signal to said muscle tissue. Thus, the method may be a method of electrical stimulation of muscle tissue. This has the further advantage that the method allows to automatically determine a suitable location for stimulation and provide a stimulation signal to the muscle tissue. This may allow to stimulate a muscle at a location suitable for stimulation even in a situation of an activated muscle, or, more generally, when the location for stimulation changes after positioning of the electrode array.

For example, in said step of activating said electrodes in accordance with a sequence of activation patterns, an electrical muscle stimulation signal may be provided to said body tissue corresponding to a stimulation intensity that is lower than a stimulation intensity corresponding to the electrical muscle stimulation signal selectively provided via the selected at least one electrode for stimulation. That is, during the search process of testing the different activation patterns, the stimulation intensity is lower than the stimulation intensity in the later step of selectively providing the stimulation signal. Thereby, interfering of the search process with the current state of the muscle tissue is minimized.

For example, the stimulation intensity in the search steps may be below a perception threshold. For example, the stimulation intensity may be just above a stimulation threshold, but low enough not to be felt.

In one embodiment, the steps of activating said electrodes in accordance with a sequence of activation patterns, measuring, alternately with said activating of electrodes in accordance with an activation pattern, a response signal associated with the activation pattern, and selecting at least one of the plurality of electrodes based on the measured response signals are repeated alternately with the step of selectively providing via the selected said at least one electrode and via said body tissue an electrical muscle stimulation signal to said muscle tissue. This allows to select electrodes corresponding to a suitable stimulation location when said location moves due to a movement, for example.

Thereby, for example, stimulation supporting a movement may be improved. For example, the method may allow to track a suitable stimulation location to support a movement.

In one embodiment, the method further comprises:
determining an orientation of a body part based on the measured response signals. For example, the orientation is an orientation relative to a specific orientation. This may have the advantage of making additional position or motion sensors, like accelerometers and gyroscopes redundant for determining an orientation of a body part.

For example, determining an orientation of the body part based on the measured response signals may comprise:
determining a state of said muscle tissue based on the measured response signals, and
determining an orientation of a body part based on the determined state of said muscle tissue.

The state of said muscle tissue is related to the orientation of said body part. For example, the orientation depends on an activation state of said muscle tissue. For example, by activating said muscle tissue, said body part may be moved. In another example, a position of a location suitable for stimulation depends on a state of the muscle tissue. For example, when an antagonist muscle is activated, said muscle tissue may be moved and, thus, the position of a location suitable for stimulation of said muscle tissue may change.

For example, the steps of activating said electrodes in accordance with a sequence of activation patterns and measuring, alternately with said activating of electrodes in accordance with an activation pattern, a response signal associated with the activation pattern, are repeated, the method further comprising:
determining a motion of a body part based on the repeatedly measured response signals.

For example, a motion of a body part may be determined by sequentially determining an orientation of the body part based on the measured response signals.

In one embodiment of the method, the step of selecting at least one of the plurality of electrodes based on the measured response signals comprises selecting at least one first electrode and at least one second electrode of the plurality of electrodes based on the measured response signals, and the step of selectively providing via said selected at least one electrode and via said body tissue an electrical muscle stimulation signal to said muscle tissue comprises selectively providing, via at least one of said selected at least one first electrode and said selected at least one second electrode, and via said body tissue, an electrical muscle stimulation signal to at least one of muscle tissue of a first muscle and muscle tissue of a second muscle.

For example, the muscle stimulation signal may be provided to muscle tissue of a muscle dependent on a state of muscle tissue of that same muscle, and/or dependent on a state of muscle tissue of a different muscle, said state being determined based on the measured response signals. This allows e.g. to improve safety of stimulation by preventing stimulation of an antagonist muscle to an activated agonist muscle. Furthermore, this allows to improve canceling undesired muscle activity, such as tremor or spasm activity, by antagonistic stimulation.

For example, the muscle stimulation signal may be provided dependent on an orientation of a body part that is determined based on the measured response signals. This facilitates stimulation of muscles to be performed in accordance with a desired motion sequence of one or more body parts.

In a further aspect of the invention, there is provided an apparatus for electrical stimulation of muscle tissue, said apparatus comprising:
an electrode array comprising a plurality of electrodes, for positioning in electrical contact with body tissue that contacts said muscle tissue; the electrode array being connectable to a signal generator for generating an electrical muscle stimulation signal;
an electrode selector for selecting from the plurality of electrodes one or more electrodes for providing the electrical stimulation signal of a connected signal generator to said body tissue;
a sensor for measuring a signal by sensing a property of said muscle tissue, which property forms a measure for activity of said muscle tissue; and
a control unit for controlling the electrode selector and for receiving a signal from the sensor, the control unit being adapted for:
activating said electrodes in accordance with a sequence of activation patterns, each activation pattern defining a subset of the electrodes to be activated, each respective subset consisting of at least one electrode, by controlling the electrode selector to select the at least one electrode of the respective subset for providing an electrical muscle stimulation signal of the signal generator to said body tissue via said at least one electrode, and,
alternately with said activating of electrodes in accordance with an activation pattern, receiving a response signal associated with the activation pattern from the sensor.

For example, the sensor may be formed by at least one of the plurality of electrodes.

For example, the electrode array is connectable to the signal generator via the electrode selector.

For example, the electrodes are electrode pads.

For example, the apparatus further comprises said signal generator.

For example, the control unit is adapted for:
activating said electrodes in accordance with a sequence of activation patterns, each activation pattern defining a subset of the electrodes to be activated, each respective subset consisting of at least one electrode, by providing an electrical muscle stimulation signal of the signal generator to said body tissue via the at least one electrode of the respective subset being selected by the electrode selector, and,
alternately with said activating of electrodes in accordance with an activation pattern, receiving a response signal associated with the activation pattern from the sensor.

For example, the control unit comprises separate units, e.g. a first control unit for controlling the electrode selector and/or the signal generator, and a second control unit for receiving the respective response signal. For example, the first control unit is an electrical muscle stimulation unit, and the second control unit is an EMG recording unit. The units can be two separate units or combined in one casing. For example, the signal generator is separate from the apparatus and is connectable to the apparatus.

In one embodiment, the control unit is further adapted for selecting at least one of the plurality of electrodes based on the response signals. For example, the control unit is further adapted for comparing the response signals associated with the respective electrodes and received by the control unit and for selecting at least one of the plurality of electrodes based on a comparison of the response signals.

In one embodiment, the apparatus further comprises a signal processing unit for analysing a response signal received from the sensor, wherein the signal processing unit is adapted for determining a criterion suitable for determining the muscle activity from the response signal. For example, the signal processing is adapted for determining at least one of:

a peak-to-peak value of the response signal,
an area under the curve of the response signal
an increase rate of the response signal, and
a decrease rate of the response signal.

The mentioned values are believed to be an indication of a magnitude of activity of the muscle tissue.

For example, the signal processing unit is adapted for outputting a value corresponding to a magnitude of an activity of the muscle tissue as represented by the measured response signal. For example, the output value may be one of the abovementioned values.

For example, the control unit is adapted for performing the method as described above.

A further aspect of the invention is the use of an apparatus as described above for the treatment of a muscle.

In a further aspect of the invention, there is provided a computer program product comprising program code portions for performing a method as described above when run on a programmable apparatus.

These and other aspects of the invention will be apparent from and illustrated with reference to the embodiments described hereinafter.

DETAILED DESCRIPTION OF EMBODIMENTS

Figure 1:
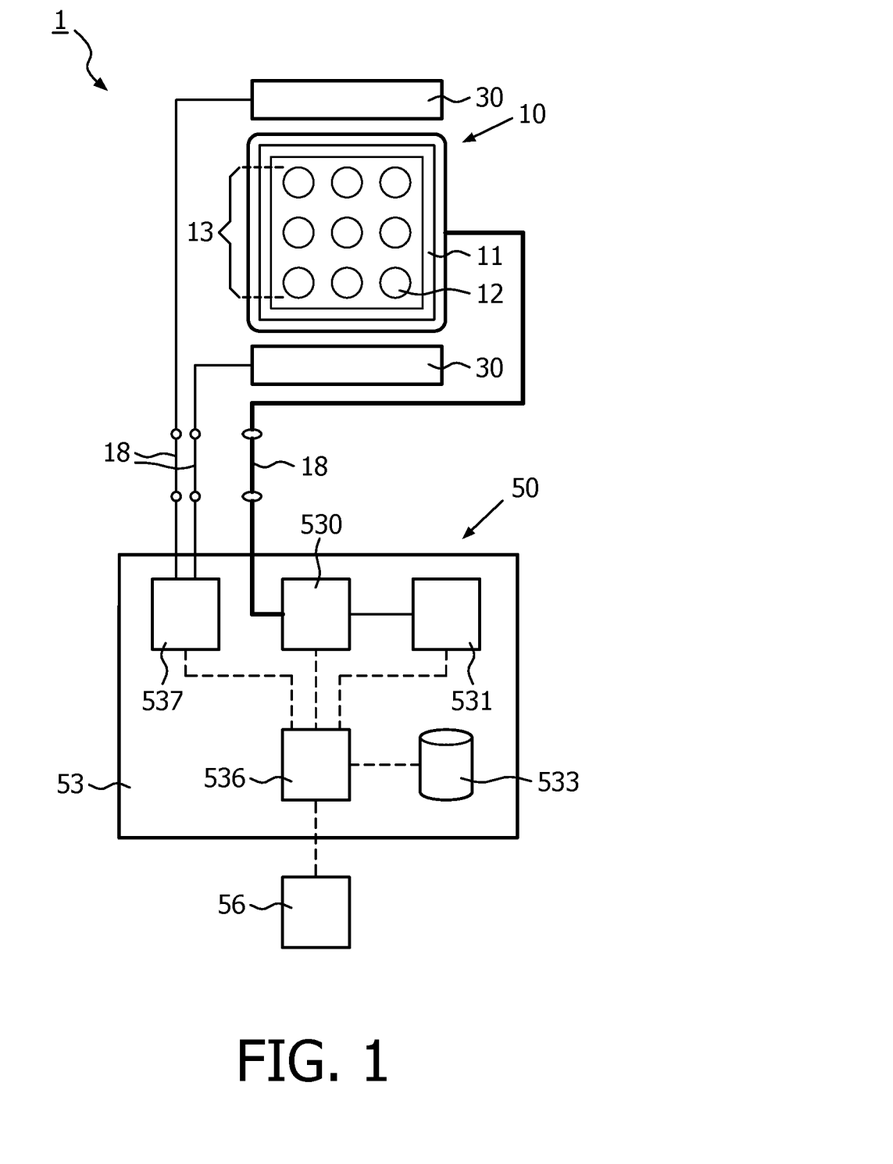
FIG. 1 shows a schematic representation of an apparatus for electrical stimulation of muscle tissue.
Figure 2:
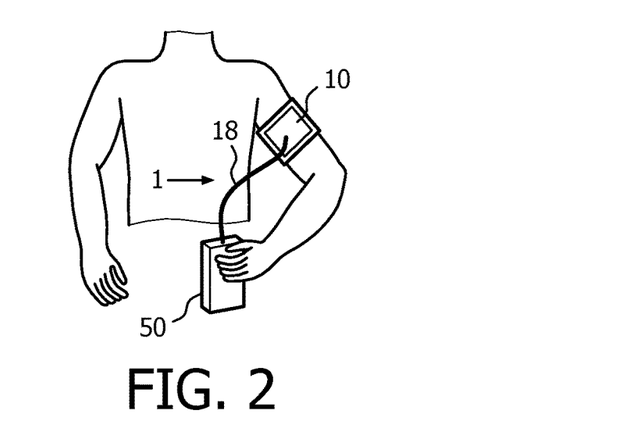
FIG. 2 schematically shows the apparatus of FIG. 1, an electrode array being placed on an upper arm of a user.

The electro-stimulation apparatus 1 shown in FIGS. 1 and 2 comprises an electrode system 10 which can be placed on the skin of an animal, such as a human being. In FIG. 2, the electrode system 10 is placed on a skin portion of the upper arm of a user. However, the electrode system 10 may be placed on another part of the body and may have a shape adapted to the shape of the specific body part. For example, in case the electrode system 10 is to be placed on the spinal area of the body, the electrode system 10 may have an elongated shape.

The electrode system 10 includes, as is shown in FIG. 1, an electrode array 13 with a plurality of electrodes 12 in the form of electrode pads. Further, in the example of FIG. 1, the electrode system includes a counter electrode 11. The counter electrode 11 acts as ground. Alternatively, for example, when stimulating via a subset of the electrodes 12, at least one other electrode 12 may act as a counter electrode or ground. Thus, the dedicated counter electrode 11 is optional.

For example, the electrodes in the electrode array 13 are positioned along straight lines, forming a rectangular matrix arrangement. In the example of FIG. 1, the matrix is a 3 by 3 matrix, however, the matrix may have other dimensions, for example smaller or larger. Further, the spacing of the columns of the matrix may be different from the spacing of the rows of the matrix. Furthermore, the matrix may, as shown in the example of FIG. 1, be square. Furthermore, the matrix may have a number of columns different from the number of rows. Furthermore, the electrodes 12 may also be positioned in a non-rectangular arrangement, such as a circular arrangement or a triangular arrangement, for example.

In the example of FIG. 1, the counter electrode 11 has a closed loop shape and encloses the electrode array 13. However, the counter electrode 11 may have a different shape and may, for example, follow a meandering path between the electrodes 12.

The electrode system 10 may be placed on the skin such that the electrodes 12 and the counter electrode 11 make electrical contact with the skin, i.e. body tissue that contacts muscle tissue below the skin. The electrode array 13 will then be electrically in contact with said muscle tissue and, in particular, will be able to receive or transmit an electrical signal to the region of the muscle below the skin area occupied by the electrode array 13. In particular, the electrodes 12 will be able to inject, via the skin, a current into the muscle tissue in the form of a muscle stimulation signal in order to stimulate the muscle tissue.

As shown in FIG. 1, the apparatus 1 further includes an operation unit 50, which is connected to the electrode array 10 via a connection 18. In the example of FIG. 1, the connection 18 is a wire connection. However, the connection 18 may also be a wireless connection. For example, the electrode system 10 may be battery powered and include a radio transmitter/receiver.

The operation unit 50 can receive signals generated by the electrode system 10 and control the operation of the electrode system 10, as is explained below in more detail.

The electrodes 12 and counter electrode 11 may be provided on a surface of a flexible, preferably resilient, carrier. This allows the electrode system to adapt to the shape of the part of the body on which the electrode system 10 is placed. The carrier may be provided with electrical components connecting the electrodes 12 and counter electrode 11, via the connection 18, to the operation unit 50.

For example, the operation unit 50 includes a housing. In the inside of the housing, a control unit 53 is provided which is connected to the electrode system 10 via the connection 18 and to an optional user interface 56. The user interface 56 may comprise, for example, a display forming an output interface for outputting information to a user of the apparatus 1 and control buttons forming an input interface. For example, the user can provide input to the control unit 53 via the user interface 56, such as for example, desired settings for the operation performed by the apparatus. In this example, the output interface allows to output data visually, however, the data may alternatively or additionally be outputted as audio or any other suitable manner.

The control unit 53 includes, as is shown in FIG. 1, an electrode selector 530 for selecting from the electrodes 12 in the electrode array 13 one or more stimulation electrodes. For example, the electrode system 10 may comprise line selector units and row selector units for addressing the electrodes 10. However, for example, the electrode system 10 may comprise electrode addressing units adapted to independently address individual electrodes 12 and combinations thereof. This enables stimulation electrodes to be selected in accordance with any activation pattern or subset of the electrodes 12 to be used for stimulation.

A signal generator 531 is connected to the electrode selector 530. In operation, the signal generator 531 provides an electrical muscle stimulation signal to the stimulation electrode pads selected by the electrode selector 530 in accordance with an activation pattern. The electrical stimulation signal is transferred via the stimulation electrodes 12 to the surface on which the electrode system 10 is placed, e.g. the skin. The electrode signal then penetrates via the skin into the muscle tissue, in response to which the muscle tissue may contract. Thereby, the muscle tissue is stimulated.

The values for the parameters of the stimulation, such as for example the amount of current and the duration of the stimulation period, may be determined by the signal generator 531 based on data stored in a memory of the signal generator 531. The signal generator 531 is connected to a programmable microprocessor 536, which is, for example, adapted to set the parameters for the stimulation. For example, the values for the parameters of the stimulation may be determined by a user via the user interface 56.

The microprocessor 536 is connected to the electrode selector 530 and is adapted to control the electrode selector 530 in order to select the stimulation electrodes in accordance with an activation pattern.

The microprocessor 536 e.g. also comprises a timer for controlling the order of operation of the microprocessor 536 such that in operation a sequence of steps of a method for providing an electrical muscle stimulation signal to body tissue via the electrode system 10 is performed as will be described below.

Furthermore, the microprocessor 536 is connected to and/or equipped with memory 533, e.g. for storing stimulation parameters or data associated with response signals as will be described below.

In the example of FIG. 1, the electrode system 10 includes a separate sensor in the form of two sensor electrodes 30. In this example, the sensor electrodes 30 extend parallel to each other on opposite sides of the electrode system 10 outside the electrode array 13 and the counter electrode 11. For example, the sensor electrodes are electrode pads forming strips of e.g. rectangular shape. In the example of FIG. 2, the sensor is a bipolar electromyography (EMG) sensor.

The sensor can sense a property of the muscle tissue, which property forms a measure for the activity of said muscle tissue. The sensor has a sensor output, which is connected to an input of a signal processing unit 537 in the control unit 53. Via the sensor output, the sensor can provide a sensor signal to the signal processing unit 537. The signal processing unit 537 can determine from the sensor signal a value of the measure for the activity, i.e. measure a signal sensed by the sensor and output the value via a processor output to the microprocessor 536. Thus, the signal processing unit 537 can output a value of a magnitude of muscle activity as represented by a measured signal to the microprocessor 536.

For example, the microprocessor 536 can determine a parameter of the muscle tissue based on the value determined by the signal processing unit 537 and output this value in a user perceptible form at the user interface 56. Furthermore, for example, an indication whether the electrode array is still positioned above the location suitable for stimulation may be generated based on the response signals, and may be indicated to the user. This is advantageous when the electrode system 10 is a dry electrode system, i.e. a system that does not adhere to the skin like "glued" electrodes, but also in the case of "glued" electrodes.

In a modified embodiment, the sensor is in the form of a single sensor electrode 30 for unipolar EMG measurement. Thus, the sensor is a unipolar EMG sensor. For example, the sensor may be arranged near the electrode array 13.

In a further modified embodiment, at least one selectable electrode of the electrodes 12 forms the sensor. For example, the electrodes 12 have a dual function of electrically stimulating muscle tissue and sensing said property of the muscle tissue, which property forms a measure for the activity of said muscle tissue. For example, the input of the signal processing unit 537 is connected to the electrodes 12, or is connectable via the electrode selector 530 to the electrodes 12. For example, at least one electrode of the electrodes 12 may act as a unipolar or bipolar EMG sensor. Thus, the separate sensor electrodes 30 are not required. For example, the control unit 53 may be adapted for controlling the electrode selector 530 to select at least one electrode 12 for forming the sensor for sensing said property of the muscle tissue via said at least one selected electrode 12, and for receiving a response signal.

Figure 3:
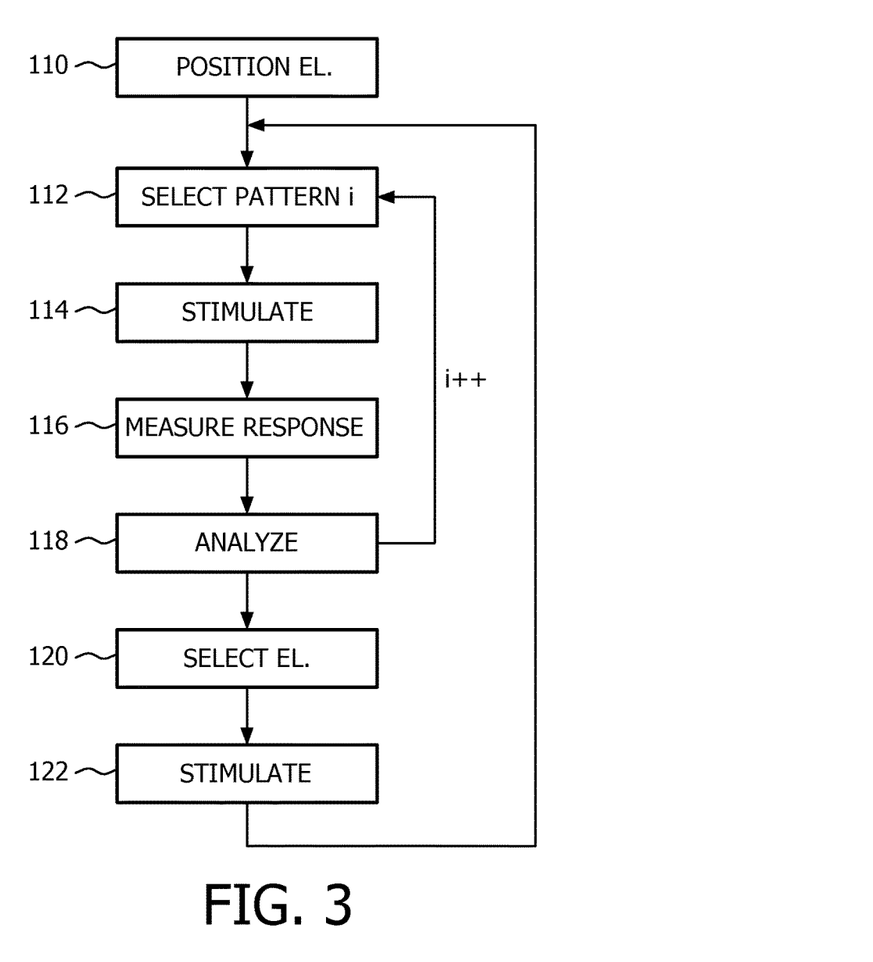
FIG. 3 shows a flow chart of a method for providing an electrical muscle stimulation signal to body tissue that contacts muscle tissue.

FIG. 3 shows a flow chart of an example of a method for providing an electrical muscle stimulation signal to body tissue that contacts muscle tissue, in particular to the skin above a muscle.

In a first step 110, the electrode system 10 comprising the electrode array 13 is positioned on a desired surface, for example a part of the skin above a muscle tissue.

In a second step 112, the microprocessor 536 controls the electrode selector 530 to select at least one stimulation electrode in accordance with a first activation pattern of a sequence of activation patterns. For example, each activation pattern may consist of a different single electrode of the electrodes 12 to be activated. For example, the sequence of activation patterns is a sequence of the electrodes in a specific order. For example, the electrodes 12 may be activated row by row and, within each row, column by column in the case of a rectangular electrode array 13. However, the microprocessor 536 may also be enabled to control the electrode selector 530 to select stimulation electrodes in accordance with an activation pattern consisting of more than one electrode.

In a third step 114, a muscle stimulation signal generated by the signal generator 531 is provided via the stimulation electrode selected by the electrode selector 530 to the skin and, thus, to the muscle tissue in electrical contact with the skin. Thereby, the muscle tissue may be electrically stimulated. The effectiveness of the stimulation usually will depend on the position of the stimulation electrode or, more generally, on the activation pattern.

In a fourth step 116, a signal of the sensor is measured by the signal processing unit 537. For example, the measuring step overlaps with the stimulating step. In particular, the signal is measured over a time span allowing to determine a magnitude of muscle activity. In particular, for example, a signal is measured during such time span after applying the stimulation signal via the stimulation electrode. Thus, the measured signal includes a response signal associated with the stimulation electrode or, more generally, the activation pattern for stimulation. For example, the signal of the sensor is continuously acquired by the signal processing unit 537, and a response signal associated with a specific stimulation electrode is identified based on information on the timing of applying the respective stimulation signals. For example, such information and, optionally, information on the activation pattern used for stimulation may be provided to the signal processing unit 537 via the microprocessor 536.

Instead of using a sensor having the sensor electrodes 30 of FIG. 1, the step of receiving a response signal associated with the activation pattern from the sensor may comprise controlling the electrode selector 530 to select at least one electrode 12 for forming the sensor for sensing said property of the muscle tissue via said at least one selected electrode 12, and receiving the response signal from the said at least one selected electrode 12.

In a fifth step 118, the signal processing unit 537 determines a value of a magnitude of muscle activity as represented by the measured response signal, as will be described below.

The search steps 112, 114, 116 and 118 are then repeated with the next activation pattern of the sequence of activation patterns being selected in step 112 and the respective at least one electrode being stimulated in step 114. The steps are repeated for each further activation pattern in the sequence of activation patterns. In the example of the activation patterns consisting of the different individual electrodes, this means that the sequence of the steps 112 to 118 is performed once for each of the nine electrodes 12. The electrodes 12 are activated one after the other, and the associated response signals are analyzed. However, the response signal measured in step 116 may also be recorded, and the steps 112 to 116 may be repeated for the sequence of activation patters, before the analyzing step 118 is performed for each response signal.

Figure 4:
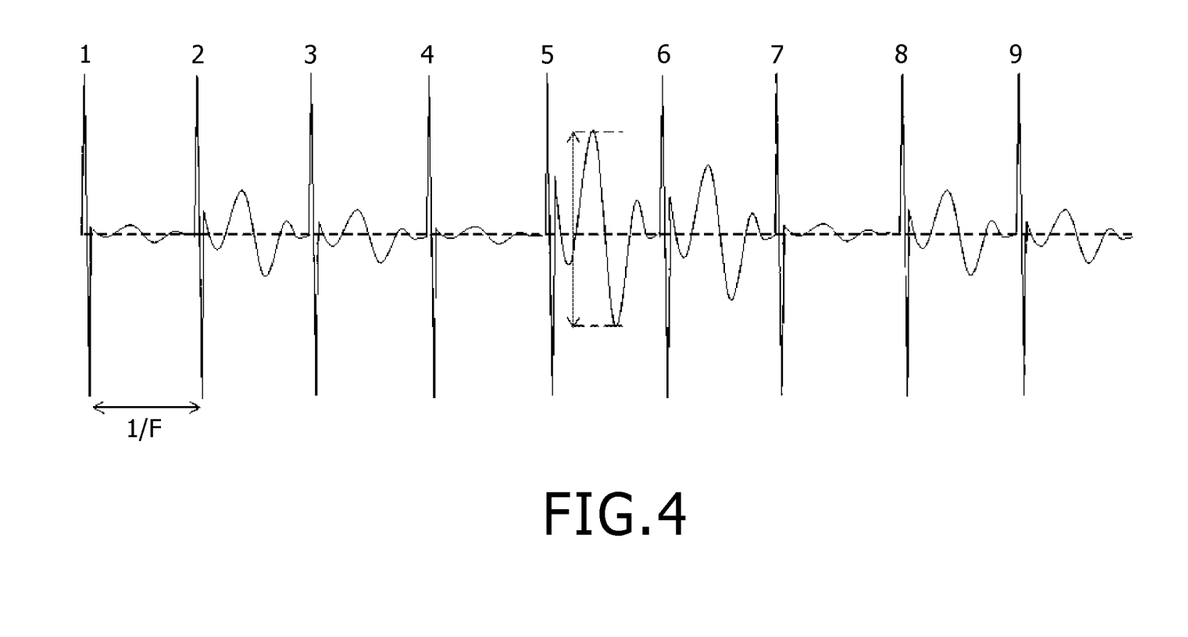
FIG. 4 schematically shows an example of EMG data.

FIG. 4 shows an example of an electromyogram (EMG) signal as received by the signal processing unit 537 from the sensor. The curve shown in FIG. 4 shows sharp peaks corresponding to the application of the stimulation signals to the individual electrodes, which are numbered in FIG. 4 from 1 to 9. In the gaps between the stimulating, a response signal associated with the respective stimulating electrode is recorded. For example, as is indicated in FIG. 4, the stimulation electrodes are sequentially activated at a frequency F.

For example, the signal processing unit 537 determines a peak to peak value for each of the response signals associated with the different stimulation electrodes or activation patterns. In FIG. 4, the maximum peak-to-peak value of the response signal associated with the electrode number 5 is indicated by a double arrow.

After a response signal for stimulation of each electrode has been measured and analyzed, at least one of the electrodes 12 is selected based on the magnitude of muscle activity as represented by the measured response signals in a sixth step 120. In particular, for example, the stimulation electrode which is found to have caused the largest magnitude of muscle activity may be selected. In the example of FIG. 4, electrode number 5 will thus be selected. In particular, for example, at least one electrode may be selected for stimulating the muscle tissue. The microprocessor 536 selects said at least one electrode. Furthermore, for example, the microprocessor 536 may control the electrode selector 530 to select said at least one electrode.

In a seventh step 122, a muscle stimulation signal of the signal generator 531 is provided via said selected at least one electrode of the electrodes 12 and via the skin to the muscle tissue in order to stimulate the muscle tissue. The electrode showing the largest magnitude of response is believed to be the electrode most suitable for stimulation of the muscle tissue. However, for example, more than one electrode may be selected for stimulation. For example, all electrodes may be selected for stimulation, the associated response signal of which show a magnitude of muscle activity above a specific threshold. In the example of FIG. 4, this may result in electrodes number 5 and 6 being selected for stimulation in step 120, these being the response signals with the largest peak to peak value.

Instead of selecting, in step 120, at least one electrode based on the criterion of a highest peak to peak value of the associated response signal, other criteria may be used for selecting the at least one electrode. Examples of suitable criteria are: the largest area under the curve of the response signal, the fastest increase rate of the response signal, a fastest decrease rate of the response signal, etc.

The method of FIG. 3 as described so far may be useful in determining electrodes for stimulating muscle tissue in a static situation of the muscle. Without wishing to be bound to any theory, it is believed that the location of the electrodes which show the largest magnitude of muscle activity in response to stimulation is the most suitable for stimulating the activity of the muscle tissue. Thus, the at least one stimulating electrode selected in step 120 corresponds to a location suitable or most suitable for stimulating said muscle tissue. Such location is expected to correspond to the motor point of the respective muscle, i.e. the area where a motor nerve enters into the muscle.

For example, in the method of FIG. 3, after stimulating the muscle tissue in step 122, the steps of the method are repeated beginning with again selecting the first stimulation electrode or activation pattern in step 112. Thus, the search process of steps 112 to 118 and the stimulation process of steps 120 and 122 are repeated. Thereby, a location suitable for stimulating the muscle tissue may be tracked in dynamic situations, for example, in a situation where the muscle contracts or relaxes or is moved due to activity of a further muscle.

For example, the search steps 112 to 116 may be performed for a sequence of activation patterns depending on a previously selected at least one stimulation electrode. For example, the search may take place on electrodes in the neighborhood of a previously selected stimulation electrode.

Thus, when the location of a motor point with respect to the skin surface changes due to an induced muscle contraction or by contraction or relaxation of muscle groups in the same body part, the described method facilitates to track the motor point in order to maintain an effective stimulation.

Furthermore, for example, a location of the motor point or the at least one stimulation electrode selected in step 120 may be displayed on a display of the user interface 56. This may allow to constantly monitor the motor point location in both static and dynamic situations.

In the described embodiment of FIG. 3, the step 120 of selecting at least one electrode for stimulation, and/or the step 122 of stimulating may be optional steps. For example, after determining at least one electrode suitable for stimulation of the muscle tissue in step 120, the method may continue with the search process of steps 112, 114, 116 and 118. This may allow to monitor the position of a location suitable for stimulation. In this case, the stimulation intensity should be as low as possible, but above the stimulation threshold; preferably low enough not to feel the search process and just above the stimulation threshold.

In another modification of the embodiment of FIG. 3, the described steps of the method may be performed simultaneously for muscle tissue of different muscles, e.g. different muscles of a muscle group. Thus, for example, steps 120 and 122 may be simultaneously or subsequently performed for stimulation of muscle tissue of different muscles. For example, in step 120, at least one first electrode may be selected for stimulation of a first muscle, and at least one second electrode may be selected for stimulation of a second muscle. For example, in step 122, there is selectively provided via the first selected at least one electrode an electrical muscle stimulation signal to muscle tissue of said first muscle, and there is selectively provided via said second selected at least one electrode an electrical muscle stimulation signal to muscle tissue of the second muscle. For example, electrodes or activation patterns associated with a large magnitude of muscle activity are assigned to at least one of the first or second or further muscles based on predetermined knowledge of the relative orientation of the locations suitable for stimulation or motor points of the different muscles. Such predetermined information may be stored in the memory 533, for example. Additionally or alternatively, such information may be gained by analyzing the muscle response for the different stimulation electrodes or activation patterns and inputting muscle data via the user interface 56. For example, in the analyzing step 118, the user may be requested to enter information on which muscle has been activated in the previous stimulation step 114. Enabling to stimulate selectively more than one muscle is advantageous especially for stimulation in an area where multiple motor points are very near to each other.

Furthermore, simultaneously performing the steps of the method of FIG. 3 for muscle tissue of different muscles may allow to relate changes of location of certain motor points to movements of other motor points or muscles. This is advantageous, for example, in a situation where the position of a motor point of a first muscle influences the position of motor points of other muscles, e.g. antagonist muscles, according to a certain dependency.

Furthermore, simultaneously performing the steps of the method of FIG. 3 for muscle tissue of different muscles is advantageous in applications like restoring the hand-grasp function, which require to stimulate different muscles in a specific sequence to achieve a desired motion of the hand. The control unit 53 may control said step 122 of selectively providing via the respective selected at least one electrode an electrical muscle stimulation signal to muscle tissue of the respective muscle according to a desired activation sequence for the different muscles. For example, the duration and time at which stimulation takes place for a specific muscle may be determined according to the desired stimulation sequence.

Furthermore, stimulation of muscle tissue of different muscles may be performed dependent on a state of an antagonist muscle to that muscle. For example, stimulation of an agonist and the respective antagonist muscle may be performed mutually exclusive. This increases the safety of muscle stimulation. Furthermore, e.g., stimulation of an agonist muscle is performed under the condition that there is no muscle activity of the antagonist muscle detected. This allows to further increase the safety of muscle stimulation.

In a further modified embodiment of the method of FIG. 3, stimulation in step 122 may be performed under the condition that activity of the antagonist muscle has been detected in the respective response signals. This may be advantageous in order to cancel a tremor or spasm movement. Thus, antagonist muscle activity, e.g. due to tremor or spasm, is measured, and the agonist muscle is stimulated in step 122 accordingly to "cancel" the tremor or spasm. For example, the steps of the method of FIG. 3 may be performed simultaneously for muscle tissue of an agonist muscle and muscle tissue of an antagonist muscle.

Figure 5:
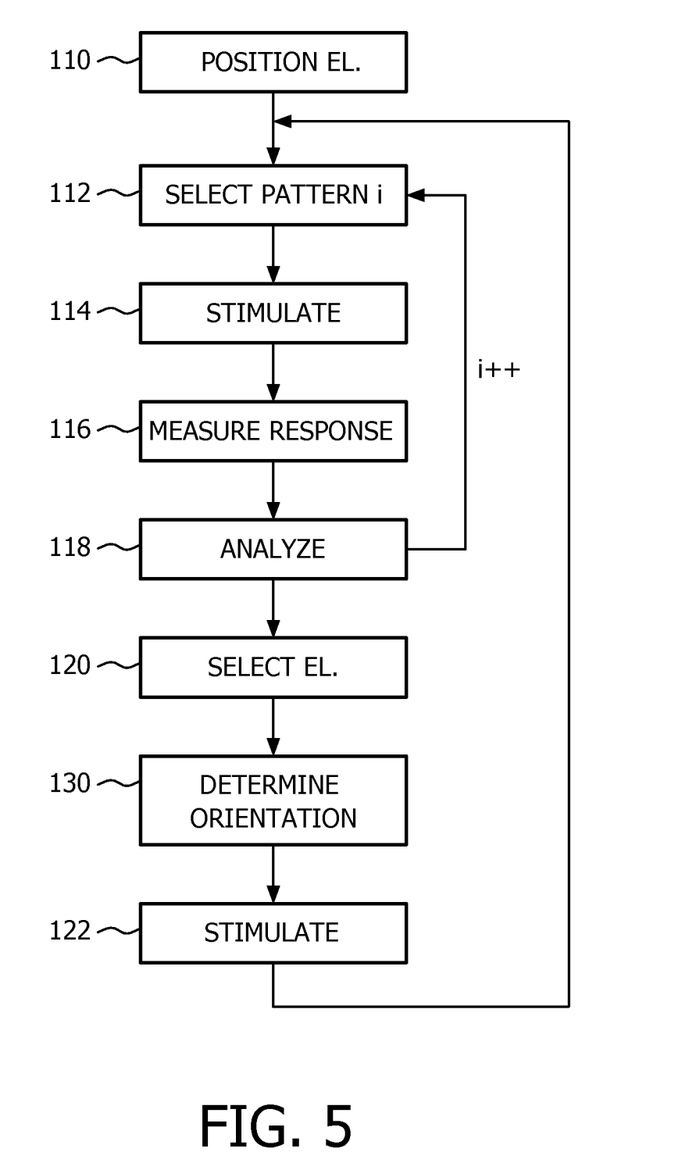
FIG. 5 schematically shows a further embodiment of a method for providing an electrical muscle stimulation signal to body tissue that contacts muscle tissue.

FIG. 5 shows a flow chart of a further example of a method for providing an electrical muscle stimulation signal to body tissue that contacts muscle tissue. The method is similar to that of FIG. 3 but differs from said method in that the stimulation step 122 is the eighth step, and between step 120 and 122, there is performed a seventh step 130 of determining an orientation of a body part based on the measured response signals.

In step 130, for example, a state of the muscle tissue is determined based on the measured response signals of step 116 and the analyzing step 118.

For example, when a location suitable for stimulation has been determined as described above, this location may be an indication of the state of the muscle. For example, said state of the muscle tissue may be a state of orientation of the muscle tissue or of a body part including said muscle tissue or of an orientation of a different body part that depends on the state of contraction or relaxation of said muscle tissue.

Furthermore, for example, in step 130, an orientation of a body part is determined, i.e. estimated, based on the determined state of said muscle tissue.

For example, the orientation of a body part is determined bases on the determined state of said muscle tissue and based on calibration data. Calibration data may be acquired in an initial calibration step where the user performs a specific movement and/or takes a specific posture and/or activates or relaxes a specific muscle. Calibration data may be stored in memory 533.

Optionally, the method is continued with the stimulating step 122, before the steps of the method are optionally repeated beginning with step 112 of the search process as described above. Thus, determining an orientation of a body part may be combined with stimulation of the muscle tissue. For example, stimulating may be performed dependent on the determined orientation. This allows, for example, to stimulate muscle tissue in accordance with a movement of a body part, e.g. adapting the stimulation as required to achieve a desired motion.

In a modified embodiment of the method of FIG. 5, the steps of the method may be performed simultaneously for muscle tissue of different muscles, similar to what has been described above with regard to the method of FIG. 3.

For example, an orientation of a body part may also be determined based on the determined state of muscle tissue of more than one muscle. For example, locations suitable for stimulation may be determined as described above for muscle tissues of more than one muscle. For example, motor points of biceps and triceps may be determined, and, in step 130, an orientation of the arm may be determined based on the determined states of these muscles.

In another example, stimulation in step 122 of the muscle tissue of the individual muscles may be performed in accordance with a sequence of muscle contraction of different muscles in order to achieve a desired motion. For example, in an application of restoring the hand-grasp function, a sequence of muscle stimulation is needed to achieve the required motion. For example, the position of the arm and/or hand and/or fingers can be determined by locating the individual muscle motor points, and a sequence of activating the different muscles may be derived from the positions or orientations determined in step 130. This has the advantage that no extra device is needed to determine the orientation of the respective body part, like e.g. an accelerometer or a gyroscope.

While the invention has been illustrated and described in detail in the drawings and foregoing description, such illustration and description are to be considered illustrative or exemplary and not restrictive. The invention is not limited to the disclosed embodiments.

In particular, each described feature of the apparatus according to the invention may be advantageously used with the method according to the invention and vice versa.

Variations to the disclosed embodiments can be understood and effected by those skilled in the art in practicing the claimed invention, from a study of the drawings, the disclosure and the appended claims.

For example, the different elements of the operation unit 50 described as being contained in a housing could as well be separate from each other, e.g. forming separate devices. Furthermore, parts of the operation unit could be included in the electrode system 10, or the operation unit could be integrated with the electrode system 10.

In the claims, the word "comprising" does not exclude other elements or steps, and the indefinite article "a" or "an" does not exclude a plurality. Any reference signs in the claims should not be construed as limiting the scope.

The invention claimed is:

1. A method of determining a location for externally stimulating a muscle of a subject, the method comprising:
    externally positioning a plurality of electrodes in electrical contact with a body tissue that contacts the muscle;
    activating at least one electrode in a first activation search pattern, the first activation search pattern defining a first subset of the plurality of electrodes consisting of at least the one electrode, such that the at least one electrode provides a first electrical muscle stimulation signal to said body tissue, wherein the first electrical muscle stimulation signal is below a muscle stimulation signal intensity implemented when applying muscle stimulation treatment after the first activation search pattern and a second activation search pattern;
    measuring a first response signal resulting from the first activation search pattern by sensing a first property of said muscle, wherein the first property is a measure of activity of said muscle caused by the first electrical muscle stimulation signal resulting from the first activation search pattern;
    activating at least one other electrode in the second activation search pattern, the second activation search pattern defining a second subset of the plurality of electrodes consisting of at least the one other electrode, such that the at least one other electrode provides a second electrical muscle stimulation signal to said body tissue, wherein the second electrical muscle stimulation signal is below the muscle stimulation signal intensity implemented when applying muscle stimulation treatment after the first activation search pattern and the second activation search pattern;
    measuring a second response signal resulting from the second activation search pattern by sensing a second property of said muscle, wherein the second property is a measure of activity of said muscle caused by the second electrical muscle stimulation signal resulting from the second activation search pattern;
    selecting a subset of the plurality of electrodes corresponding to the first or second activation search pattern based on a largest measure of activity of the muscle as determined in the first and second response signals; and
    applying the muscle stimulation signal intensity for treatment according to the selected subset of the plurality of electrodes, wherein the muscle stimulation signal intensity for treatment is a muscle stimulation signal intensity at a magnitude that contracts and relaxes muscle tissue.

2. The method as claimed in claim 1, the method further comprising:
    selecting at least one of the plurality of electrodes such that the selected at least one of the plurality of electrodes corresponds to at least one suitable stimulation location.

3. The method as claimed in claim 2, further comprising: determining an orientation of a body part based on the first or second measured response signals.

4. The method as claimed in claim 3, wherein the at least one suitable location is indicative of an orientation of the body part including the muscle, or of an orientation of a different body part that depends on a state of contraction or relaxation of the muscle, and wherein the orientation of a body part is determined based on the at least one suitable location.

5. The method as claimed in claim 3, further comprising acquiring calibration data while the subject performs a specific movement, or takes a specific posture, or activates or relaxes a specific muscle, and wherein the calibration data is used in the step of determining the orientation of a body part.

6. The method as claimed in claim 1, the method further comprising determining at least one further suitable stimulation location, for stimulating a further muscle of the subject, based on the first or second measured response signal and on information on which muscle the electrical muscle stimulation signal was provided to.

7. An apparatus for external electrical stimulation of a muscle of a subject, the apparatus comprising:
    a plurality of electrodes, for positioning externally and in electrical contact with a body tissue that contacts said muscle, the plurality of electrodes being connectable to a signal generator for generating an electrical muscle stimulation signal;
    an electrode selector for selecting from the plurality of electrodes one or more electrodes for providing the electrical muscle stimulation signal of a connected signal generator to said body tissue;
    a sensor for measuring a signal by sensing a property of said muscle, wherein the property is a measure of activity of said muscle caused by the electrical muscle stimulation signal; and
    a control unit for controlling the electrode selector and for receiving a signal from the sensor, the control unit being configured for:
    activating at least one electrode in a first activation search pattern, the first activation search pattern defining a first subset of the plurality of electrodes consisting of at least the one electrode, by controlling the electrode selector to select the at least one electrode to provide a first electrical muscle stimulation signal of the signal generator to said body tissue, wherein the first electrical muscle stimulation signal is below a muscle stimulation signal intensity implemented when applying muscle stimulation treatment after the first activation search pattern and a second activation search pattern;
    receiving a first response signal resulting from the first activation search pattern from the sensor which senses a first property of the muscle, wherein the first property is a measure of activity of the muscle caused by the first electrical muscle stimulation signal resulting from the first activation search pattern;
    activating at least one other electrode in the second activation search pattern, the second activation search pattern defining a second subset of the plurality of electrodes consisting of at least the one other electrode, by controlling the electrode selector to select the at least one other electrode to provide a second electrical muscle stimulation signal of the signal generator to said body tissue, wherein the second electrical muscle stimulation signal is below the muscle stimulation signal intensity implemented when applying muscle stimulation treatment after the first activation search pattern and the second activation search pattern;

receiving a second response signal resulting from the second activation search pattern from the sensor which senses a second property of the muscle, wherein the second property is a measure of activity of the muscle caused by the second electrical muscle stimulation signal resulting from the second activation search pattern;

selecting a subset of the plurality of electrodes corresponding to the first or second activation search pattern based on a largest measure of activity of the muscle as determined by the first and second response signals; and applying the muscle stimulation signal intensity for treatment according to the selected subset of the plurality of electrodes, wherein the muscle stimulation signal intensity for treatment is a muscle stimulation signal intensity at a magnitude that contracts and relaxes muscle tissue.

8. The apparatus as claimed in claim 7, wherein the control unit is further adapted for selecting at least one of the plurality of electrodes such that the selected at least one of the plurality of electrodes corresponds to at least one first suitable stimulation location or at least one second suitable stimulation location.

9. A non-transitory computer readable medium embedded with program code portions for performing a method according to claim 1 when run on a programmable apparatus.

* * * * *